United States Patent
Balkenhohl et al.

(10) Patent No.: US 6,234,811 B1
(45) Date of Patent: May 22, 2001

(54) METHOD FOR PRODUCING ESTERS OF TRIAZOLOPYRIMIDINE DERIVATIVES FREE OF ENANTIOMERS USING VINYLESTERS WITH LIPASE

(75) Inventors: Friedhelm Balkenhohl, Limburgerhof; Stefan Koser, Ludwigshafen, both of (DE); Nicholas John Holman, Nottingham (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/319,875
(22) PCT Filed: Feb. 9, 1998
(86) PCT No.: PCT/EP98/00709
 § 371 Date: Jun. 14, 1999
 § 102(e) Date: Jun. 14, 1999
(87) PCT Pub. No.: WO98/37225
 PCT Pub. Date: Aug. 27, 1998

(30) Foreign Application Priority Data

Feb. 19, 1997 (DE) .............................. 197 06 337

(51) Int. Cl.$^7$ ...................................... C12P 17/18
(52) U.S. Cl. .......................................... 439/119; 435/280
(58) Field of Search ..................... 435/119, 280

(56) References Cited

U.S. PATENT DOCUMENTS 4,963,492  10/1990  Keller et al. .

FOREIGN PATENT DOCUMENTS 605 033  7/1994  (EP) .
95/10521  4/1995  (WO) .

OTHER PUBLICATIONS

Tet. Lts. vol. 27, No. 43, 5241–5244, 1986, Akita et al.
Tetrahedron: Asymmetry, vol. 3, No. 7, 827–830, 1992 Seemayer et al.

*Primary Examiner*—Sandra E. Saucier
(74) *Attorney, Agent, or Firm*—Keil & Weinkauf

(57) ABSTRACT

A process for preparing enantiomerically pure esters of the formula I (Ia and Ib)

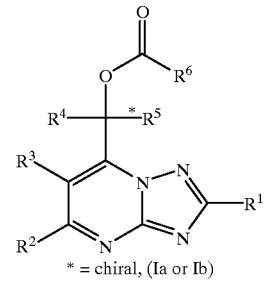

\* = chiral, (Ia or Ib)

where the substituents have the following meanings:
$R^1$
hydrogen or substituted or unsubstituted $C_1-C_6$-alkyl, $C_1-C_6$-alkoxy or $Cl-C_6$-alkanoyl,
$R^2$ and $R^3$
independently of one another hydrogen or substituted or unsubstituted $C_1-C_6$-alkyl, $C_1-C_6$-alkoxy, $C_1-C_6$-alkanoyl, $C_1-C_6$-alkylthio, $C_1-C_6$-alkylsulfinyl or $C_1-C_6$-alkylsulfonyl,
$R^4$ and $R^5$
$R^4 \ne R^5$ and independently of one another hydrogen or substituted or unsubstituted $C_1-C_6$-alkyl or $R^4$ and $R^5$ form together with the carbon atoms to which they are bonded a substituted or unsubstituted $C_3-C_6$-cycloalkylidene,
$R^6$
substituted or unsubstituted aryl, $C_1-C_{20}$-alkyl, $C_3-C_{20}$-alkenyl, $C_3-C_{20}$-alkynyl, $C_1-C_{20}$-alkoxy-$C_1-C_{20}$-alkyl
comprises converting racemic compounds of the formula II,

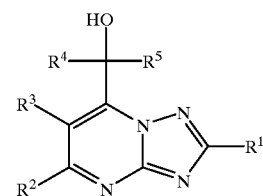

where the substituents $R^1$ to $R^5$ have the abovementioned meanings, with a lipase or esterase in the presence of vinyl esters of the formula III,

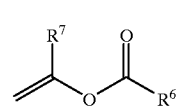

where $R^6$ has the abovementioned meaning, and $R^7$ is hydrogen or methyl, into compounds of the formula I.

9 Claims, No Drawings

METHOD FOR PRODUCING ESTERS OF TRIAZOLOPYRIMIDINE DERIVATIVES FREE OF ENANTIOMERS USING VINYLESTERS WITH LIPASE

BACKGROUND OF THE INVENTION

The invention relates to a process for preparing enantiomerically pure alcohols.

Kinetic resolutions of racemic esters with lipases and esterases are described in a large number of publications and patents. Only a few studies on the resolution of racemic esters or alcohols which have a heteroaromatic radical have been published.

Thus, for example, Akita et al. (Tetrahedron Lett. 27 (1986), No. 43, 5241–5244) describe the enantioselective hydrolysis of methyl 3-acetoxy-3-(2-furyl)-2-methylpropanoates or methyl 3-acetoxy-3-(2-thienyl)-2-methylpropanoates with an Aspergillus niger lipase.

De Amici et al. describe, in J. Org. Chem. 54 (1989) 2646–2650, an enzymatically catalyzed transesterification with porcine liver esterase, Candida cylindracea lipase, chymotrypsin, subtilisin, porcine pancreatic lipase and lipase P.

Tsukamoto et al. (Tetrahedron Asym. 2 (1991), No. 8,759–762) describe the synthesis of (R)- and (S)-N,N-diethyl-2,2-difluoro-3-(2-furyl)-3-hydroxypropionamide from the corresponding esters with Candida cylindracea lipase MY and P in water.

DE/OS 3743824 and Schneider et al. (Tetrahedron Asym. 3 (1992), No. 7, 827–830) describe the preparation of 1-pyridylethanol.

The disadvantages of these methods are the low selectivity of the enzymes, the low enantiomeric purities of the products obtained, the low chemical yields, and the large amounts of enzyme required for the reaction.

An optimal racemate resolution should advantageously comply with a number of conditions, such as:

1. high enantiomeric purity of the antipodes
2. high chemical yield
3. high enzyme selectivity
4. small amounts of catalyst (amounts of enzyme)
5. good solubility of precursor and product under the reaction conditions
6. good space-time yield
7. easy purification of the products
8. low-cost synthesis.

WO 95/10521 claims 1,2,4-triazolo[1,5-a]pyrimidines, their chemical synthesis and their use in pharmaceutical compositions.

BRIEF SUMMARY OF THE INVENTION

It is an object of the present invention to develop a stereoselective synthesis of intermediates for 1,2,4-triazolo-[1,5-a]pyrimidines which provides these compounds advantageously with high optical purities and good chemical yields and which permits easy workup of the products.

DETAILED DESCRIPTION OF THE INVENTION

We have found that this object is achieved by a process for preparing enantiomerically pure esters of the formula I (Ia or Ib)

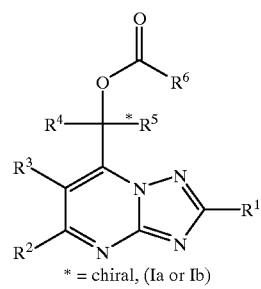

* = chiral, (Ia or Ib)

where the substituents have the following meanings:

$R^1$ hydrogen or substituted or unsubstituted $C_1$–$C_6$-alkyl, $C_3$–$C_6$-alkoxy or $C_1$–$C_6$-alkanoyl, $R^2$ and $R^3$ independently of one another hydrogen or substituted or unsubstituted $C_1$–$C_6$-alkyl, $C_1$–$C_6$-alkoxy, $C_1$–$C_6$-alkanoyl, $C_1$–$C_6$-alkylthio, $C_1$–$C_6$-alkylsulfinyl or $C_1$–$C_6$-alkylsulfonyl, $R^4$ and $R^5$ $R^4 \neq R^5$ and independently of one another hydrogen or substituted or unsubstituted $C_1$–$C_6$-alkyl or $R^4$ and $R^5$ form together with the carbon atoms to which they are bonded a substituted or unsubstituted $C_3$–$C_6$-cycloalkylidene, $R^6$ substituted or unsubstituted aryl, $C_1$–$C_{20}$-alkyl, $C_3$–$C_{20}$-alkenyl, $C_3$–$C_{20}$-alkynyl, $C_1$–$C_{20}$-alkoxy-$C_1$–$C_{20}$-alkyl which comprises converting racemic compounds of the formula II,

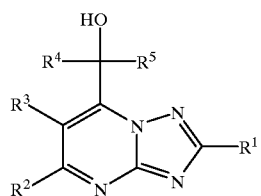

where the substituents $R^1$ to $R^5$ have the abovementioned meanings, with a lipase or esterase in the presence of vinyl esters of the formula III,

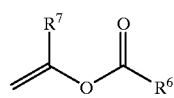

where $R^6$ has the abovementioned meaning, and $R^7$ is hydrogen or methyl, into compounds of the formula I.

$R^1$ in the formulae I and II is hydrogen or substituted or unsubstituted $C_1$–$C_6$-alkyl, $C_1$–$C_6$-alkoxy or $C_1$–$C6$-alkanoyl.

Examples of meanings for the radicals mentioned for $R^1$ are the following:

alkyl branched or unbranched C1-C$_6$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, alkoxy branched or unbranched $C_1$–$C_6$-alkoxy chains as mentioned above, eg. methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-l-methylpropoxy or 1-ethyl-2-methylpropoxy, alkanoyl branched or unbranched $C_1$–$C_6$-alkanoyl chains such as methanoyl, ethanoyl, propanoyl, 1-methylethanoyl, butanoyl, 1-methylpropanoyl, 2-methylpropanoyl, 1,1-dimethylethanoyl, pentanoyl, 1-methylbutanoyl, 2-methylbutanoyl, 3-methylbutanoyl, 1,1-dimethylpropanoyl, 1,2-dimethylpropanoyl, 2,2-dimethylpropanoyl, 1-ethylpropanoyl, hexanoyl, 1-methylpentanoyl, 1,2-methylpentanoyl, 3-methylpentanoyl, 4-methylpentanoyl, 1,1-dimethylbutanoyl, 1,2-dimethylbutanoyl, 1,3-dimethylbutanoyl, 2,2-dimethylbutanoyl, 2,3-dimethylbutanoyl, 3,3-dimethylbutanoyl, 1-ethylbutanoyl, 2-ethylbutanoyl, 1,1,2-trimethylpropanoyl, 1,2,2-trimethylpropanoyl, 1-ethyl-1-methylpropanoyl and 1-ethyl-2-methylpropanoyl.

Suitable substituents for the alkyl, alkoxy or alkanoyl radicals mentioned for $R^1$ are one or more substituents such as halogen such as fluorine, chlorine, bromine, cyano, nitro, amino, mercapto, alkyl, alkoxy or aryl.

$R^2$ and $R^3$ in the formulae I and II are, independently of one another, hydrogen or substituted or unsubstituted $C_1$–$C_6$-alkyl, $C_1$–$C_6$-alkoxy, $C_1$–$C_6$-alkanoyl, $C_1$–$C_6$-alkylthio, $C_1$–$C_6$-alkylsulfinyl or $C_1$–$C_6$-alkylsulfonyl.

Examples of meanings of the radicals mentioned for $R^2$ and $R^3$ are the following:

alkyl branched or unbranched $C_1$–$C_6$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-l-methylpropyl or 1-ethyl-2-methylpropyl, alkoxy branched or unbranched $C_1$–$C_6$-alkoxy chains as mentioned above, eg. methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-l-methylpropoxy or 1-ethyl-2-methylpropoxy, alkanoyl branched or unbranched $C_1$–$C_6$-alkanoyl chains such as methanoyl, ethanoyl, propanoyl, 1-methylethanoyl, butanoyl, 1-methylpropanoyl, 2-methylpropanoyl, 1,1-dimethylethanoyl, pentanoyl, 1-methylbutanoyl, 2-methylbutanoyl, 3-methylbutanoyl, 1,1-dimethylpropanoyl, 1,2-dimethylpropanoyl, 2,2-dimethylpropanoyl, 1-ethylpropanoyl, hexanoyl, 1-methylpentanoyl, 1,2-methylpentanoyl, 3-methylpentanoyl, 4-methylpentanoyl, 1,1-dimethylbutanoyl, 1,2-dimethylbutanoyl, 1,3-dimethylbutanoyl, 2,2-dimethylbutanoyl, 2,3-dimethylbutanoyl, 3,3-dimethylbutanoyl, 1-ethylbutanoyl, 2-ethylbutanoyl, 1,1,2-trimethylpropanoyl, 1,2,2-trimethylpropanoyl, 1-ethyl-1-methylpropanoyl and 1-ethyl-2-methylpropanoyl, alkylthio branched or unbranched $C_1$–$C_6$-alkylthio chains such as methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, alkylsulfinyl branched or unbranched $C_1$–$C_6$-alkylsulfinyl chains such as methylsulfinyl, ethylsulfinyl, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl, alkylsulfonyl branched or unbranched $C_1$–$C_6$-alkylsulfonyl chains such as methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

Suitable substituents for the alkyl, alkoxy, alkanoyl, alkylthio, alkylsulfinyl or alkylsulfonyl radicals mentioned for $R^2$ and $R^3$ are one or more substituents such as halogen such as fluorine, chlorine, bromine, cyano, nitro, amino, mercapto, alkyl, alkoxy or aryl.

$R^4$ and $R^5$ are not the same and in the formulae I and II are, independently of one another, hydrogen or substituted or unsubstituted $C_1$–$C_6$-alkyl or $R^4$ and $R^5$ form together with the carbon atoms to which they are bonded a substituted or unsubstituted $C_3$–$C_6$-cycloalkylidene.

Examples of meanings of the radicals mentioned for $R^4$ and $R^5$ are the following:

alkyl branched or unbranched $C_1$–$C_6$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, cycloalkylidene branched or unbranched $C_3$–$C_6$-cycloalkylidene chains such as cyclopropylidene, ethylcyclopropylidene, dimethylcyclopropylidene, methylethylcyclopropylidene, cyclobutylidene, ethylcyclobutylidene, dimethylcyclobutylidene, cyclopentylidene or methylcyclopentylidene.

Suitable substituents for the alkyl or cycloalkylidene radicals mentioned for $R^4$ and $R^5$ are one or more substituents such as halogen such as fluorine, chlorine, bromine, cyano, nitro, amino, mercapto, alkyl, alkoxy or aryl.

$R^6$ in the formulae I and III is substituted or unsubstituted aryl, $C_1$–$C_{20}$-alkyl, $C_1$–$C_{20}$-alkenyl, $C_1$–$C_{20}$-alkynyl or $C_1$–$C_{20}$-alkoxy-$C_1$–$C_{20}$-alkyl.

Examples of meanings for the radicals mentioned for $R^6$ are the following:

aryl simple or fused aromatic ring systems which are unsubstituted or substituted by one or more radicals such as halogen such as fluorine, chlorine or bromine, cyano, nitro, amino, mercapto, alkyl, alkoxy or other saturated or unsaturated nonaromatic rings or ring systems, or are unsubstituted or substituted by at least one other $C_1$–$C_{10}$-alkyl chain, or are linked via a $C_1$–$C_{10}$-alkyl chain to the basic framework, and phenyl and naphthyl are preferred as aryl radical, alkyl branched or unbranched $C_1$–$C_{20}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tetradecyl, n-hexadecyl, n-octadecyl or n-eicosyl, and Cl-$C_8$-alkyl chains are preferred, $C_2$–$C_4$-alkyl chains are particularly preferred and substituted $C_2$–$C_4$-alkyl chains are very particularly preferred (see below for substituents), such as chloroethyl or methoxyethyl, alkenyl branched or unbranched $C_3$–$C_{20}$-alkenyl chains such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-l-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-l-propenyl, 1-ethyl-2-propenyl, 1-hexenyl, 2-hexenyl, 3-hexenyl, 4-hexenyl, 5-hexenyl, 1-methyl-1-pentenyl, 2-methyl-b 1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-l-butenyl, 2,3-dimethyl-2-butenyl, 2,3-dimethyl-3-butenyl, 3,3-dimethyl-l-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-l-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl or 7-octenyl, and unsaturated alkyl chains which can be derived from natural fatty acids, such as mono- or polyunsaturated $C_{16}$-, $C_{18}$- or C20-alkyl chains are preferred, alkynyl branched or unbranched $C_3$–$C_{20}$-alkynyl chains such as prop-1-yn-1-yl, prop-2-yn-1-yl, n-but-l-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl or 4-methyl-pent-2-yn-5-yl, and $C_3$-$C_{10}$-alkynyl chains are preferred, and $C_3$-$C_6$-alkynyl chains are particularly preferred.

alkoxyalkyl branched or unbranched $C_1$-$C_{20}$-alkoxy-$C_1$-$C_{20}$-alkyl chains such as methoxymethyl, methoxyethyl, methoxypropyl, ethoxymethyl, propoxymethyl, 1-methylethoxymethyl, butoxymethyl, 1-methylpropoxymethyl, 2-methylpropoxymethyl, 1,1-dimethylethoxymethyl, and $C_1$-$C_{10}$-alkoxy-$C_1$-$C_{10}$-alkyl is preferred, $C_1$-$C_6$-alkoxy-$C_1$-$C_8$-alkyl is particularly preferred and $C_1$-$C_4$-alkoxy-$C_1$-$C_4$-alkyl is very particularly preferred. Likewise preferred are α,β-saturated alkoxyalkyl radicals.

Suitable substituents for the alkyl, alkenyl, alkynyl or alkoxyalkyl radicals mentioned for $R^6$ are one or more substituents such as halogen such as fluorine, chlorine, bromine, cyano, nitro, amino, mercapto, alkyl, alkoxy or aryl.

The enzymes suitable in principle for the process according to the invention are all lipases or esterases of nomenclature class 3.1—which react with ester linkages. However, lipases or esterases of microbial origin or porcine pancreatic lipase are preferred. Examples of enzymes of microbial origin which may be mentioned are enzymes from fungi, yeasts or bacteria such as Alcaligenes sp., Achromobacter sp., *Aspergillus niger, Bacillus subtilis, Candida cylindracea, Candida lypolytica, Candida antarctica*, Candida sp., *Chromobacterium viscosum*, Chromobacterium sp., *Geotrichum candidum, Humicola lanuginosa, Mucor miehei, Penicillium camemberti, Penicillium roqueforti, Phycomyces nitens, Pseudomonas cepacia, Pseudomonas glumae, Pseudomonas fluorescens, Pseudomonas plantarii, Pseudomonas aeruginosa*, Pseudomonas sp., *Rhizopus arrhizus, Rhizopus delemar, Rhizopus japanicus, Rhizopus niveus, Rhizopus oryzae* or Rhizopus sp. Particularly preferred lipases or esterases are those from Pseudomonas species such as *Pseudomonas cepacia* or *Pseudomonas plantarii*, from Candida species such as *Candida cylindracea* or *Candida antarctica*, such as Novozym® 435 or porcine pancreatic lipase. Very particularly preferred are Pseudomonas plantarii lipase, Amano P® lipase (supplied by Amano, Japan), NovozymSP523, SP524, SP525, SP526, SP539, SP435 (supplied by Novo, Denmark), Chirazyme® L1, L2, L3, L4, L5, L6, L7, L8, E1 (supplied by Boehringer Mannheim, Germany), porcine pancreatic lipase or the lipase from Pseudomonas spec. DSM 8246.

The enzymes are employed in the reaction directly or as immobilizates on a wide variety of carriers. The amount of enzyme to be added depends on the nature of the precursor, product, the vinyl ester and the activity of the enzyme preparation. The optimal amount of enzyme for the reaction can easily be determined by simple preliminary tests. The enzyme/substrate ratio, calculated as molar ratio between enzyme and substrate, depends on the enzyme and is, as a rule, from 1:1000 to 1:50000000 or more, preferably 1:100000 to 1:5000000, which means that it is possible, for example to cleave 3 kg or more of a substrate with a molecular weight of about 100 to its enantiomers using 10 mg of an enzyme. The enantioselectivity (=E) of the enzymes is, as a rule, advantageously from 20 to 1000 in this case.

The enzymes can be used directly in the reaction as free or immobilized enzymes or else, advantageously, after an activation step in aqueous medium in the presence of a surface-active substance such as oleic acid, linoleic acid or linolenic acid and subsequent removal of water.

The enzyme reaction can be carried out without adding additional solvents or solvent mixtures only in the presence of the vinyl esters (see formula III) as solvent. It is advantageous to add other solvents or solvent mixtures to the reaction. Suitable for this in principle are all aprotic or protic solvents. All solvents inert in the reaction are suitable, that is they must not take part in the enzyme reaction. Unsuitable examples are primary or secondary alcohols, DMF, DMSO and water because side reactions may occur in the presence of these solvents—they are enzyme substrates themselves or lead to hydrolysis of the esters—and/or the enzymes tend to stick together and thus the enzyme activity decreases drastically. DMF and DMSO damage enzymes in prolonged reactions, presumably due to removal of the hydrate sheath around the enzymes. Examples of suitable solvents which may be mentioned here are pure aliphatic or aromatic hydrocarbons such as hexane, cyclohexane or toluene, halogenated hydrocarbons such as methylene chloride or chloroform, ethers such as MTBE, THF, diethyl ether, diisopropyl ether or dioxane, tertiary alcohols such as tert-butanol, tert-pentyl alcohol or propylene carbonate, ethylene carbonate or acetonitrile. It is advantageous to have additional solvents or solvent mixtures present, particularly preferably to have toluene, diethyl ether, diisopropyl ether or tert-pentyl alcohol present. The solvents used for this purpose should be as anhydrous as possible in order to prevent unspecific hydrolysis of the esters. The activity of water in the reaction can advantageously be controlled by using molecular sieves or ammonium salts.

All vinyl esters are suitable in principle for the reaction, such as the vinyl esters of long-chain fatty acids ($C_{12}$ to $C_{20}$), vinyl chloroacetate, vinyl acetate, vinyl propionate or vinyl butyrate, and vinyl acetate, vinyl propionate or vinyl butyrate is preferably used, and vinyl propionate or vinyl butyrate is particularly preferably used.

The reaction is advantageously carried out at from 0° C. to 75° C., preferably from 10° C. to 60° C., particularly preferably from 15° C. to 50° C.

The reaction times are from 1 to 72 hours depending on the substrate, ester and enzyme. From 1 to 3 mol of vinyl ester are added per mole of substrate to be reacted.

The course of the reaction can easily be followed by conventional methods, for example by gas chromatography. It is sensible to stop the reaction when 50% of the racemic alcohol has reacted—maximum yield with maximum enantiomeric purity in theory. The reaction may be stopped earlier or later, that is before or after 50% of the racemate has reacted, to increase the enantiomeric purity. This usually takes place by removing the catalyst from the reaction . . . , for example by filtering off the enzyme.

Depending on the enzyme there is selective formation of the R or S ester (see formula I, claim 1 and formulae Ia and Ib in scheme I which depict the individual enantiomers). The other enantiomer in each case does not react and remains unchanged at the alcohol stage (see formulae IIa and IIb in Scheme I, which depict the two enantiomers of the alcohols). Scheme I shows by way of example the synthesis of one enantiomer of the ester in reaction 1, and the other possible synthetic processes for converting the wrong enantiomer into the required enantiomer in reactions 2 to 6.

Scheme I Processes for Preparing Enantiomerically Pure Esters of the Formula I (R enantiomer or S enantiomer, Ia or Ib)

sulfonic anhydrides with mesylates, tosylates or brosylates and hydrolysis, or reaction with carboxylates, or converted into the required enantiomer in a reaction to form trichloroacetimidates and subsequent reaction with, for example, carboxylic acids or carboxylates, and subsequently esterified.

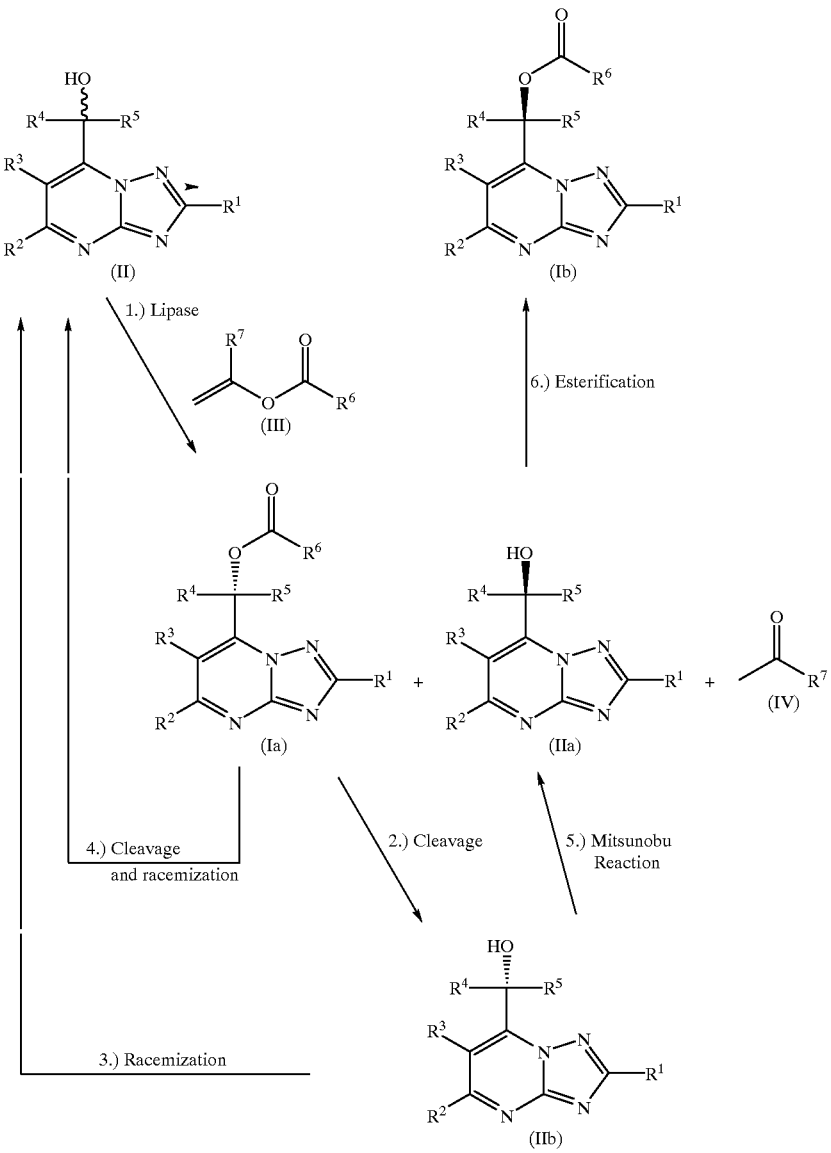

If the ester (Ia) produced in the first reaction (Scheme I) is the required enantiomer, this is separated from the other reaction products (IIa and IV). This can take place, for example, by precipitating the alcohol (IIa) in a nonpolar solvent such as toluene and subsequently filtering. The ester remains in the organic phase, and the latter can be extracted with water to remove the remaining alcohol. The unwanted alcohol enantiomer can then be either racemized after removal of IV, for example by basic treatment, and recycled, or else converted directly to the esters in a chemical reaction with inversion of the stereocenter, for example in a Mitsunobu reaction (see Scheme I), or in a reaction to form If the ester (Ia) produced in the first reaction (Scheme I) is the unwanted enantiomer, this is removed from the other reaction products (IIa and IV) for example as described above. The ester can then be either cleaved with retention of the stereochemistry to the alcohol (IIb) (reaction 2, aminolysis or hydrolysis), racemized and recycled (reaction 3) or cleaved with racemization and recycled (reaction 4) or else converted, after cleavage (reaction 2), in a subsequent chemical reaction in which the stereocenter is inverted into the required enantiomer of the alcohol (IIa) (reaction 5). The desired enantiomer of the alcohol (IIa) can finally be esterified to the required ester (reaction 6).

EXAMPLES

Examples 1 to 10

The enzymes used as shown in Scheme II were assayed with the following mixture:

0.25 mmol of precursor
2.0 ml of THF or MTBE, dioxane
0.25 mmol of vinyl propionate
25 mg of enzyme Scheme II Stereoselective esterification with vinyl esters

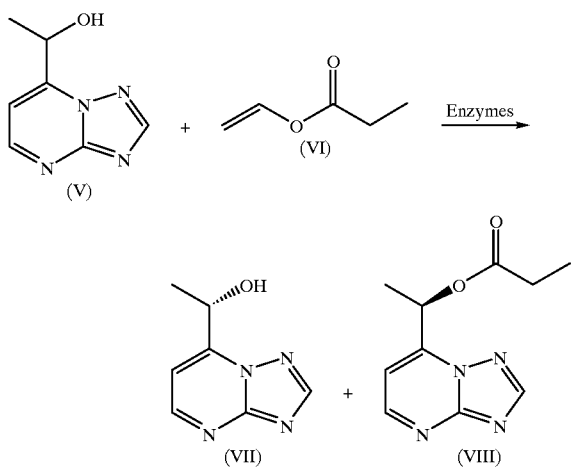

For the short assays, the enzymes were weighed into screw-cap tubes. The reaction was started by adding precursor (V) and vinyl propionate (VI) in THF or MTBE/dioxane. The mixtures were incubated at room temperature (23° C.) with stirring (magnetic stirrer, 150 rpm). Samples were taken for TLC analysis after 4 h and 24 h (TLC analysis, mobile phase ethyl acetate: methanol 10:1, UV analysis). The optical rotation was determined on mixtures which showed conversion in this rapid assay (optical rotation measurement: $[\alpha]^{25°\ C.}$/Na in ethanol, c=1).

TABLE I

Optical rotations measured with various enzymes

| Mixture | Enzyme | Rotation after 4 h | Rotation after 24 h |
|---|---|---|---|
| 1 | Lipase from Pseudomonas spec. DSM 8246 | −0.428 | −0.352 |
| 2 | Novozym ® SP525 | — | −0.019 |
| 3 | Novozym ® SP526 | — | +0.031 |
| 4 | Subtilisin | — | — |
| 5 | Novozym ® SP435 | −0.089 | −0.335 |
| 6 | Chirazyme ® L1 | −0.241 | −0.561 |
| 7 | Chirazyme ® L2 | — | −0.091 |
| 8 | Chirazyme ® L4 | −0.334 | −0.314 |
| 9 | Chirazyme ® L5 | — | +0.034 |
| 10 | Chirazyme ® L6 | −0.297 | −0.338 |

The activities of the enzymes mentioned in the assay with vinyl propionate and the precursor varied widely in the rapid assay (Experiments 1 to 10). Both enantiomers are formed.

Example 11

To determine the kinetics of enantiomer formation, the following larger mixture was carried out with the best enzyme from Experiments 1 to 10 (Chirazyme® L1):

10 mmol of precursor
80 ml of THF
10 mmol of vinyl propionate
410 mg of enzyme

The precursor (V) was introduced together with the vinyl propionate (VI) into THF. The reaction was started by adding the enzyme. Samples were taken, and the optical rotation was measured, after incubation at room temperature (23° C.) for 2, 4, 6, 8, 24, 28 and 96 h. The reaction was at a standstill after 96 h, i.e. there was no further shift between the two enantiomers (ester and alcohol) present in the reaction after 96 h.

TABLE II

Optical rotations measured with Chirazyme ® L1

| Time in h | Optical rotation |
|---|---|
| 2 | −0.056 |
| 4 | −0.091 |
| 6 | −0.128 |
| 8 | −0.161 |
| 24 | −0.342 |
| 28 | −0.358 |
| 96 | −0.561 |

Example 12

In order to determine the enantiomeric purity of the individual components, a mixture was carried out as described in Example 11, and the enantiomers (VII and VIII) were separated from one another by precipitating the alcohol in toluene and removing the organic phase and washing it several times with water. The enantiomeric purities of the alcohol and of the ester after cleavage with retention of the stereocenter were determined after formation of the Mosher ester (see Scheme III).

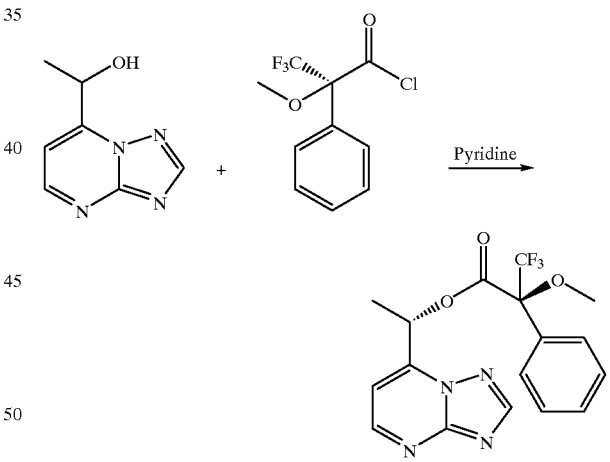

The enantiomerin purity of the two enantiomers was also determined on an HPLC column (Chiracel OD 250×4 mm, eluent 900 ml of n-hexane, 100 ml of isopropanol, 1 ml of diethylamine, 10 ml of methanol, gradient: isocratic, flow rate: 1.0 ml/min, pressure: 28 bar, UV 254 nm, running time: 35 min, sample: 1 mg/5 ml of eluent).

The enantiomeric purity of the ester (VIII) was determined to be 99.1% ee by HPLC and 85% ee using the Mosher ester, and that of the alcohol to be 66.1% ee with 40% conversion. The enzntiosectivity (E) of the enzyme was E =467.

Example 13

Conversion of the precursor with lipase from Pseudomonas spec. DSM 8246 in the following mixture:

2.5 mmol of precursor 20 ml of THF or MTBE/dioxane 2.5 mmol of vinyl propionate 82 mg of lipase from P. spec. DSM 8246

The mixture was incubated with shaking (150 rpm) at room temperature (23° C). The enantiomeric purity determined by HPLC for the ester was 97.5% ee and for the alcohol was 60% ee, with 38.1% conversion.

Example 14

The conversions and enantiomeric purities were determined as described in Example 12 with the other enzymes Chirazym® L4 and L6. The enantiomeric purity for L4 was 99.5% ee for the ester and 62.5% ee for the alcohol, with 38.6% conversion (E=652). In order to be able to measure the enantiomeric purities of the two components at exactly 50% conversion, the reaction was carried out under HPLC control and the reaction was stopped at exactly 49.2% conversion. Under these conditions, the enantiomeric purity for the enzyme L6 was 99.4% ee for the ester and 96.1% ee for the alcohol (E=1417).

Example 15

Conversion of the precursor with lipase from Pseudomonas spec. DSM 8246 in a larger mixture:

505 mmol of precursor 2500 ml of THF 505 mmol of vinyl propionate 8.3 g of lipase from P. spec. DSM 8246

The reaction was started by adding the lipase. The experiment was carried out as described in Example 12. 99.65 g of product were isolated after workup. The enantiomeric purities were determined to be as follows: ester 97% ee, alcohol >98% ee.

We claim:

1. A process for preparing enantiomerically pure esters of the formula I

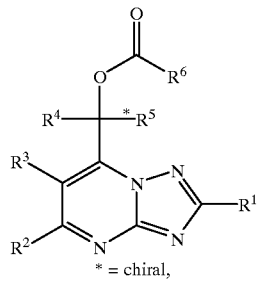

where the substituents have the following meanings:

$R^1$ hydrogen or substituted or unsubstituted $C_1$–$C_6$-alkyl, $C_1$–$C_6$-alkoxy or $C_1$–$C_6$-alkanoyl, $R^2$ and $R^3$ independently of one another hydrogen or substituted or unsubstituted $C_1$–$C_6$-alkyl, $C_1$–$C_6$-alkoxy, $C_1$–$C_6$-alkanoyl, $C_1$–$C_6$-alkylthio, $C_1$–$C_6$-alkylsulfinyl or $C_1$–$C_6$-alkylsulfonyl, $R^4$ and $R^5$ $R^4 \neq R^5$ and independently of one another hydrogen or substituted or unsubstituted $C_1$–$C_6$-alkyl or $R^4$ and $R^5$ form together with the carbon atoms to which they are bonded a substituted or unsubstituted $C_3$–$C_6$-cycloalkylidene, $R^6$ substituted or unsubstituted aryl, $C_1$–$C_{20}$-alkyl, $C_3$–$C_{20}$-alkenyl, $C_3$–$C_{20}$-alkynyl, $C_1$–$C_{20}$-alkoxy-$C_1$–$C_{20}$-alkyl which comprises converting racemic compounds of the formula II,

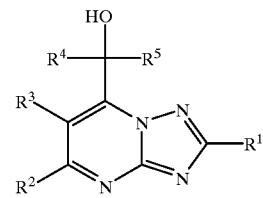

where the substituents $R^1$ to $R^5$ have the abovementioned meanings, with a lipase or esterase in the presence of vinyl esters of the formula III,

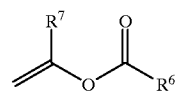

where $R^6$ has the abovementioned meaning, and $R^7$ is hydrogen or methyl, into compounds of the formula I.

2. The process as claimed in claim 1, wherein the process is carried out in the presence of at least one inert solvent.

3. The process as claimed in claim 1, further comprising removing the alcohol of the formula II produced in the reaction.

4. The process as claimed in claim 1, further comprising cleaving the enantiomerically pure compounds of the formula 1, with retention of the stereochemistry, to compounds of the formula II.

5. The process as claimed in claim 1, further comprising racemizing the enantiomer of the formula II which is unwanted in each case and the recemate is returned to the reaction.

6. The process as claimed in any of claim 1, further comprising cleaving the enantiomerically pure compounds of the formula II to compounds of the formula II and returning the cleaved compounds to the reaction.

7. The process as claimed in claim 1, further comprising converting the particular unwanted enantiomerically pure compound of the formula II in a chemical reaction with inversion of the stereocenter into the required enantiomer.

8. The process as claimed in claim 1, wherein the enantiomerically pure compound of the formula II are esterified with retention of the stereochemistry to compounds of the formula I.

9. The process as claimed in claim 1, wherein a lipase or esterase of microbial origin or a porcine pancreatic lipase is used.

* * * * *

UNITED STATES PATENT AND TRADEMARK OFFICE
CERTIFICATE OF CORRECTION

PATENT NO.    : 6,234,811 B1
DATED         : May 22, 2001
INVENTOR(S)   : Balkenhohl et al.

Page 1 of 1

It is certified that error appears in the above-identified patent and that said Letters Patent is hereby corrected as shown below:

ABSTRACT
Fourth line after formula (I), "C1-$C_6$-alkanoyl" should be -- $C_1$-$C_6$-alkanoyl --.

Column 14, claim 6,
Line 48, "formula II", first occurrence, should be -- formula I --.

Signed and Sealed this

Eighteenth Day of December, 2001

Attest:

*Attesting Officer*

JAMES E. ROGAN
*Director of the United States Patent and Trademark Office*